(12) United States Patent
Katti et al.

(10) Patent No.: US 8,586,096 B2
(45) Date of Patent: *Nov. 19, 2013

(54) SOY OR LENTIL STABILIZED GOLD NANOPARTICLES AND METHOD FOR MAKING SAME

(75) Inventors: Kattesh K. Katti, Columbia, MO (US); Raghuraman Kannan, Columbia, MO (US); Kavita K. Katti, Columbia, MO (US); Nripen Chanda, Columbia, MO (US); Ravi Shukla, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 370 days.

This patent is subject to a terminal disclaimer.

(21) Appl. No.: 12/241,904

(22) Filed: Sep. 30, 2008

(65) Prior Publication Data

US 2009/0117045 A1 May 7, 2009

Related U.S. Application Data

(60) Provisional application No. 60/997,160, filed on Oct. 1, 2007.

(51) Int. Cl.
| | |
|---|---|
| B82Y 5/00 | (2011.01) |
| A61K 49/00 | (2006.01) |
| B32B 15/04 | (2006.01) |
| H05B 6/64 | (2006.01) |
| A61P 43/00 | (2006.01) |
| A61K 9/14 | (2006.01) |

(52) U.S. Cl.
USPC .......................................................... 424/490

(58) Field of Classification Search
None
See application file for complete search history.

(56) References Cited

U.S. PATENT DOCUMENTS

| | | | |
|---|---|---|---|
| 5,541,289 A | 7/1996 | Gilbertson | |
| 6,103,868 A | 8/2000 | Heath et al. | |
| 6,572,673 B2 | 6/2003 | Lee et al. | |
| 6,818,199 B1 | 11/2004 | Hainfeld et al. | |
| 2005/0054613 A1 | 3/2005 | Katti et al. | |
| 2006/0234248 A1* | 10/2006 | Sun et al. | ........................ 435/6 |
| 2007/0051202 A1 | 3/2007 | Raghuraman et al. | |

FOREIGN PATENT DOCUMENTS

| | | |
|---|---|---|
| WO | WO 03/072053 | 9/2003 |
| WO | WO 2007/027978 | 3/2007 |
| WO | WO 2009/005752 | 1/2009 |

OTHER PUBLICATIONS

Markowitz et al. (Journal of Colloid and Interface Science 210, 73-85 (1999)).*

Rai et al. (Critical Reviews in Biotechnology, 28:277-284, 2008).*
Balogh, Lajos P. Shraddha S. Nigavekar, Andrew C. Cook, Leah Minc, Khan, Mohamed K., "Development of dendrimer-gold radioactive nanocomposites to treat cancer microvasculature," *Biotechnology*, vol. 2, No. 4, 2003, pp. 94-44.
Santanu Bhattacharya et al. "Synthesis of gold nanoparticles stabilised by metal-chelator and the controlled formation of close-packed aggregates by them," Proc. Indian Acad. Sci. (Chem. Sci), vol. 115, Nos. 5 & 6, Oct.-Dec. 2003, pp. 613-619.
Brust M., Walker M., Bethell D., Schiffrin D.J., Whyman R., "Synthesis of Thiol-Derivatised Gold Nanoparticles in a Two-Phase Liquid-Liquid System", *Journal of the Chemical Society—Chemical Communications*, vol. 7, 1994, pp. 801-802.
Chen J., Saeki F., Wiley B.J., Cang H., Cobb M.J,. Li Z-Y, et al. "Gold Nanocages: Bioconjugation and Their Potential Use as Optical Imaging Contrast Agents", *Nano Letters*, vol. 5, No. 3, 2005; pp. 473-477.
Jorge Gardea-Torresdey, "Plants with Midas Touch: Formation of Gold Nanoparticles by Alfalfa Plants," Believed published circa 2002 on the World Wide Web at: http://www-ssrl.slac.stanford.edu/research/highlights_archive/alfalfa.html.
Gierada, D. S.; Bae, K. T., "Gadolinium as a CT contrast agent: Assessment in a porcine model", *Radiology*, vol. 210, 1999, pp. 829-834.
Hainfeld, J. F.; Slatkin, D. N.; Focella, T. M.; Smilowitz, H. M., "Gold nanoparticles: a new X-ray contrast agent", *British Journal of Radiology*, vol. 79, 2006, pp. 248-253.
S. He et al., "Superlattices of Silver Nanoparticles Passivated by Mercaptan," *Journal of Physics D: Applied Physics*, vol. 34, 2001, pp. 3425-3429.
L. Kalaugher, "Green Technique Makes Silver Nanoparticles,", www.nanotechweb.org/articles/news/3/1/1/1, Jan. 2004.
Kannan R, Rahing V, Cutler C, Pandrapragada R, Katti KK, Kattumuri V, et al., "Nanocompatible chemistry toward fabrication of target-specific gold nanoparticles", *Journal of the American Chemical Society*, vol. 128, No. 35, 2006; pp. 11342-11343.
Kattumuri, V.; Katti, K.; Bhaskaran, S.; Boote, E. J.; Casteel, S. W. et al., "Gum arabic as a phytochemical construct for the stabilization of gold nanoparticles: In vivo pharmacokinetics and X-ray-contrast-imaging studies", *Small*, vol. 3, No. 2, 2007, pp. 333-341.
Kattumuri V, Chandrasekhar M, Guha S, Raghuraman K, Katti K.V, Ghosh K, et al., "Agarose-stabilized gold nanoparticles for surface-enhanced Raman spectroscopic detection of DNA nucleosides", *Applied Physics Letters*, vol. 88, No. 15, 2006, pp. 153114-1-153114-3.
Beomseok Kim et al., "Tuning the Optical Properties of Large Gold Nanoparticle Arrays," *Mat. Res. Soc. Symp. Proc.*, vol. 676, 2001.
Beomseok Kim et al., "Self-Organization of Large Gold Nanoparticle Arrays," *J. Am. Chem. Soc.*, vol. 123, 2001, pp. 7955-7956.

(Continued)

*Primary Examiner* — Patricia A Duffy
*Assistant Examiner* — Garen Gotfredson
(74) *Attorney, Agent, or Firm* — Greer, Burns & Crain Ltd.

(57) ABSTRACT

The invention provides stabilized, biocompatible gold nanoparticles that are stabilized with material from soy or lentil plant material or a reactive extract thereof of the plant material. The gold nanoparticles of the invention can be fabricated with an environmentally friendly method for making biocompatible stabilized gold nanoparticles. In methods of the invention, an aqueous solution containing gold salts is mixed with soy or lentil plant material or a reactive extract thereof. In preferred embodiment methods of making, an aqueous solution containing gold salts is provided. The aqueous solution is mixed with soy or lentil plant material or a reactive extract thereof. The gold salts react to form biocompatible gold nanoparticles that are stabilized with a robust coating derived of the soy or lentil plant material or a reactive extract thereof.

20 Claims, 3 Drawing Sheets

(56) References Cited

OTHER PUBLICATIONS

I. Pastoriza-Santos et al.. "Reduction of Silver Nanoparticles in DMF. Formation of Monolayers and Stable Colloids,", *Pure Appl. Chem.*, vol. 72, Nos. 1-2, 2002, pp. 83-90.
Peters R., "Nanoscopic medicine: The next frontier", *Small* vol. 2, No. 4, 2006 pp. 452-456.
Kandikere Ramaiah Prabhu et al. "De novo synthetic design for air-stable *bis* primary phosphines: Synthetic, catalytic and biomedical motifs," Special Section: Non-Metal Chemistry; Current Science, vol. 78, No. 4, Feb. 25, 2000.
Rosset, A.; Spadola, L.; Ratib, O., "OsiriX: An open-source software for navigating in multidimensional DICOM images", *Journal of Digital Imaging*, vol. 17. No. 3, 2004, pp. 205-216.
Sokolov K, Aaron J, Hsu B, Nida D, Gillenwater A, Follen M, et al., "Optical systems for In vivo molecular imaging of cancer", *Technology in Cancer Research & Treatment*, vol. 2, No. 5, 2003, pp. 487-594.
Spring, D. B.; Barkan, H. E.; Bettmann, M. A., Dr Spring and colleagues respond: Safety of ionic and nonionic contrast media, *Radiology*, vol. 206, 1998, pp. 560-561.
Spring, D. B.; Bettmann, M. A.; Barkan, H. E., "Nonfatal adverse reactions to iodinated contrast media: Spontaneous reporting to the U.S. Food and Drug Administration, 1978-1994", *Radiology*, vol. 204, 1997, pp. 325-332.
Spring, D. B.; Bettmann, M. A.; Barkan, H. E., "Deaths related to iodinated contrast media reported spontaneously to the U.S. Food and Drug Administration, 1978-1994: Effect of the availability of low-osmolality contrast medial", *Radiology*, vol. 204, 1997, pp. 333-337.
Volkert, W.A., T.J. Hoffman, "Therapeutic Radiopharmaceuticals," *Chem. Rev.*, vol. 99, No. 9; pp. 2269-2292, (1999).
Wagner V, Dullaart A, Bock AK, Zweck A., "The emerging nanomedicine landscape", *Nature Biotechnology*, vol. 24, No. 10, 2006; pp. 1211-1217.
Yin et al., "Synthesis and Characterization of Stable Aqueous Dispersion of Silver Nanoparticles Through the Tollens Process," *J. Mater. Chem.*, vol. 12, 2002, pp. 522-527.
RadiologicalSocietyofNorthAmerica Computed Tomography (CT). http://www.radiologyinfo.org/en/info.cfm?pg=bodyct, (2011).
ImaginisMedicalResource http://www.imaginis.com/ct-scan/, (2011).
MedCompare Contrast Agents. http://www.medcompare.com/matrix/165/Contrast-Agents.html, (2011).

\* cited by examiner

SOY OR LENTIL STABILIZED GOLD NANOPARTICLES AND METHOD FOR MAKING SAME

PRIORITY CLAIM AND REFERENCE TO RELATED APPLICATION

The application claims priority under 35 U.S.C. §119 from prior provisional application Ser. No. 60/997,160, which was filed on Oct. 1, 2007.

STATEMENT OF GOVERNMENT INTEREST

This invention was made with government support under contract no. R01CA 119412 awarded by the National Cancer Institute. The government has certain rights in the invention.

FIELD

A field of the invention is gold nanoparticles. Example applications of the invention include medical diagnostics and medical therapies. Non-medical applications include sensors and electronic materials. Gold nanoparticles find use as therapeutic agents, sensors, electronic materials and coatings on biological and non-biological surfaces.

BACKGROUND

Nanomedicine is an emerging area of medicine that utilizes nanoparticles for the detection and treatment of various diseases and disorders. Nanoparticles are tiny fragments of metals (or non metals) that are 100,000 times smaller than the width of human hair. Nanoparticles typically have different properties than naturally occurring bulk materials. Collateral properties emanate when materials, especially metals, are reduced to dimensions measured in nanometers. Nanoparticles exhibit properties that are unique from their corresponding naturally occurring bulk material.

Nanoparticles within the size range of about 1-50 nanometers have a size that can be correlated to cells, viruses, proteins and antibodies. The size resemblance that such nanoparticles have to living cells and cell components are of great interest to medical research because cells are primary components of all life (humans and animals).

Gold nanoparticles have a number of important potential medical applications. One application is hyperthermia treatment in which gold nanoparticles are heated with oscillating magnetic fields after being associated with a targeted cell, typically cancer cells. Other applications relate to biological imaging, as gold nanoparticles display photo absorbance or emission characteristics that can be used in imaging for the diagnosis of various diseases. Contrast enhancement is also provided by gold nanoparticles. For example, the selective absorption of X-rays by gold and other metallic nanoparticles provides measurable contrasts for use in computer tomographic (CT) imaging and other imaging techniques These and other important diagnostic and therapeutic properties are attainable only when metallic (or non metallic) materials are reduced to nanometer particle sizes.

Gold nanoparticles have unique properties that make them more attractive than other nanoparticles for many therapeutic, imaging, and sensing applications, and particularly in medical applications. Gold nanoparticles have an unoxidized state, whereas most of the surface of less noble metals get oxidized to a depth of several nanometers or more, often significantly reducing or obliterating the nanoscale properties of the nanoparticles. Gold nanoparticles are highly reactive, but biocompatible, making them especially well-suited for in vivo imaging and therapy. Gold nanoparticles can also be coated with specific biomolecules including, monoclonal antibodies, aptamers, peptides and various receptor specific substrates. Receptor specific coated nanoparticles are used mainly for targeting three different markers that are over expressed on cancer cells. They include: matrix metalloproteases, epidermal growth factor receptor, and oncoproteins that are associated with human papillomavirus infection.

For such in vivo imaging and therapy applications, it is that gold nanoparticles be produced stabilized in a biologically benign medium. Many current methods of producing gold nanoparticles require the removal of unreacted chemicals and byproducts from the nanoparticles as the chemicals and byproducts are necessary to the synthesis of the gold nanoparticles. The chemicals and byproducts must be removed after the production of nanoparticles to make the nanoparticles biocompatible.

Typical known methods of making nanoparticles utilize harsh conditions, such as the application of sodium borohydride to reduce $AuCl_4^-$. See, e.g., M. Brust et al, "Synthesis of Thiol-Derivatized Gold Nanoparticles in a 2-Phase Liquid-Liquid System" Journal of the Chemical Society-Chemical Communications (7):801-02 (1994). The method provides for the efficient production of gold nanoparticle, but is unsuitable in the presence of target specific peptides because sodium borohydride will reduce chemical functionalities present on peptide backbones, which can reduce or eliminate the biospecificity of biomolecules. The sodium borohydride reduction method also uses thiols to stabilize the gold nanoparticles from agglomeration. Thiol-gold nanoparticle interaction is strong and makes gold nanoparticles highly stable. Once the gold nanoparticles are stabilized by thiols, they cannot be readily transferred onto useful drug moieties including peptides, proteins and various biochemical vectors that are normally used to target diagnostic and therapeutic gold nanoparticles on to tumor and various disease sites in the body. Other methods that have been developed utilize chemical cocktails during nanoparticle production, and are not environmentally friendly in additional to having the drawbacks concerning stabilization, reactivity, and biocompatibility.

Soya bean (aka soybeans) and lentils have been part of human/animal diet for many centuries. Soy has many health benefits due to the presence of soy-proteins and isoflavones genistein and daidzein. Soy and lentils contain protease inhibitors, flavonoids, isoflavones, polyphenols, terpenes, saponins, phytosterols, phytate and a host of phytochemicals. Flavonoids are polyphenolic constituents of soybeans and lentils with antioxidant properties by virtue of the structural arrangements and hydrogen-donating potential of their phenolic groups. Synergistic effects of polyphenols and isoflavonoid compounds, specifically genistein and daidzein, have been implicated in the prevention of various cancers. Regular consumption of soy and lentils appears, according to a number of studies, to inhibit carcinogenesis. Genistein found in soy and various lentils has been linked to an antibody against B cells led to long-term survival in leukemic mice by killing of cancer cells. Several studies have shown that Soy isoflavones have the ability to slow down the development of prostate cancer. There is experimental evidence suggesting that when isoflavones are digested, equol is formed. Equol blocks the functioning of dihydrotestosteron (DHT) resulting in a reduced prostate cancer risk. However, for measurable chemopreventive effects, large quantities of soy products are necessary to be effective against prostate cancer. Recommended doses range from 1.5-2 litres of soy milk or 250 grams of soy burger daily. Soy and lentils are also effective as antioxidant agents. In particular the antioxidant properties of isoflavonoids-radical scavenging, antioxidant antiestrogenic antimutagenic, antiproliferative differentiation-inducing and angiogenesis-inhibiting activities have provided greater awareness on the introduction of soy and lentils within the human food chain.

SUMMARY OF THE INVENTION

The invention provides stabilized, biocompatible gold nanoparticles that are stabilized with material from soy or lentil plant material or a reactive extract thereof of the plant material. The gold nanoparticles of the invention can be fabricated with an environmentally friendly method for making biocompatible stabilized gold nanoparticles. In methods of the invention, an aqueous solution containing gold salts is mixed with soy or lentil plant material or a reactive extract thereof. In preferred embodiment methods of making, an aqueous solution containing gold salts is provided. The aqueous solution is mixed with soy or lentil plant material or a reactive extract thereof. The gold salts react to form biocompatible gold nanoparticles that are stabilized with a robust coating derived of the soy or lentil plant material or a reactive extract thereof.

DETAILED DESCRIPTION OF THE PREFERRED EMBODIMENTS

The invention provides stabilized, biocompatible gold nanoparticles that are stabilized with material from soy or lentil plant material or extracted reactive extracts of soy or lentil material. The gold nanoparticles of the invention can be fabricated with an environmentally friendly method for making biocompatible stabilized gold nanoparticles. In methods of the invention, an aqueous solution containing gold salts is mixed with soy or lentil plant material or extracted reactive extracts of soy or lentil material.

Fabrication methods of the invention require only gold salts as precursors. No other man-made chemicals are employed in the overall fabrication process, and there are accordingly no harsh chemicals utilized in the fabrication or harsh byproducts formed during the fabrication. Fabrication processes of the invention are therefore environmentally friendly and biologically benign.

Gold nanoparticles produced by methods of the invention demonstrate a high affinity for cancer cells/tissue. Embodiments of the invention include the diagnostic and therapeutic use of gold nanoparticles produced by methods of the invention in molecular imaging and therapy of cancer and various diseases in animals and human subjects.

Preferred embodiment of the invention are gold nanoparticles that are stabilized with extracts from soybean, lentils and beans or similar naturally occurring materials. Example preferred embodiments for making gold nanoparticles include steps of reacting a gold salt with soy or lentil plant based materials or reactive extracts thereof to produce biocompatible gold nanoparticles. Exemplary soy or lentil plant based materials include soybeans and lentils.

In a preferred method of fabrication, soybeans and lentils or reactive extracts thereof are used to produce well defined gold nanoparticles by direct interaction with gold salts. The method produces gold nanoparticles that require no further purification and are therefore biocompatible for use in biomedical and non medical applications. Gold nanoparticles produced by the method of the invention are stabilized and are suitable for use within the body (in vivo) for diagnostic imaging using X-ray contrast CT imaging for the detection of various diseases, disorders and cancer. The gold nanoparticles are also suitable as X-ray enhancers in X-ray therapy of diseases including cancer. The gold nanoparticles are also useful for localized heating of targeted cells, namely hyperthermia treatment. Gold nanoparticles of the invention are biologically benign and therefore are useful as coatings on skin, hair, for direct injections into specific tissue, for ingestion, etc. Gold stabilized nanoparticles of the invention have biocompatible properties that are suitable for use in clinical CT imaging, X-ray induced cancer therapy and in combinations of various gold nanoparticles mediated diagnosis and therapy of various diseases including cancer in animals and human beings.

Gold nanoparticles of the invention are biocompatible for direct administration in the body through oral or intravenous routes for the detection and therapy of various diseases including cancer in animals and human beings. Stabilized, biocompatible gold nanoparticles of the invention possess inherent high affinity toward gastrin releasing peptide (GRP) receptors present on cancerous cells of the prostate, breast and various types. This affinity makes the stabilized, biocompatible gold nanoparticles very well-suited for many diagnostic and therapeutic techniques. The stabilized, biocompatible gold nanoparticles of the invention interact have been shown in experiments to interact very strongly with cancerous cells (prostate, breast, small lung cancer, non-small lung cancer, liver cancer and various malignant tumors that affect animals and human beings). The stabilized, biocompatible gold nanoparticles internalize within such cells.

Preferred embodiments will now be discussed with respect to the drawings. The description includes descriptions of experiments. The drawings include schematic figures that are not to scale, which will be fully understood by skilled artisans with reference to the accompanying description. Features may be exaggerated for purposes of illustration. From the preferred embodiments and experiments, artisans will recognize additional features and broader aspects of the invention.

An example embodiment environmentally friendly method of producing gold nanoparticles uses direct interaction of sodium tetrachloaurate or aurochloric acid with naturally available soybeans and lentils. In this embodiment, production of stabilized, biocompatible gold nanoparticles is achieved by simple suspension of soybeans or lentils to an aqueous solution of aurochloric acid or sodium tetrachloroaurate. Gold nanoparticles produced by this process did not require any external chemical to generate or stabilize the gold nanoparticles. Various phytochemicals present in soybeans or lentils are believed to be responsible for making a robust coating on the stabilized, biocompatible gold nanoparticles.

Figure 1:
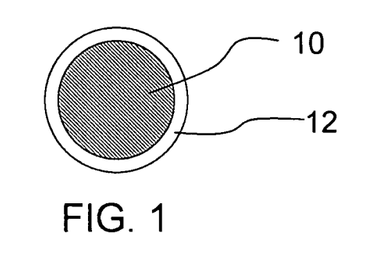
FIG. 1 is a schematic diagram that illustrates a stabilized, biocompatible gold nanoparticle of the invention.

FIG. 1 is a schematic diagram that illustrates a stabilized, biocompatible gold nanoparticle of the invention. In FIG. 1, a gold nanoparticle 10 is coated with a layer derived of soy or lentil plant material 12.

Figure 2:
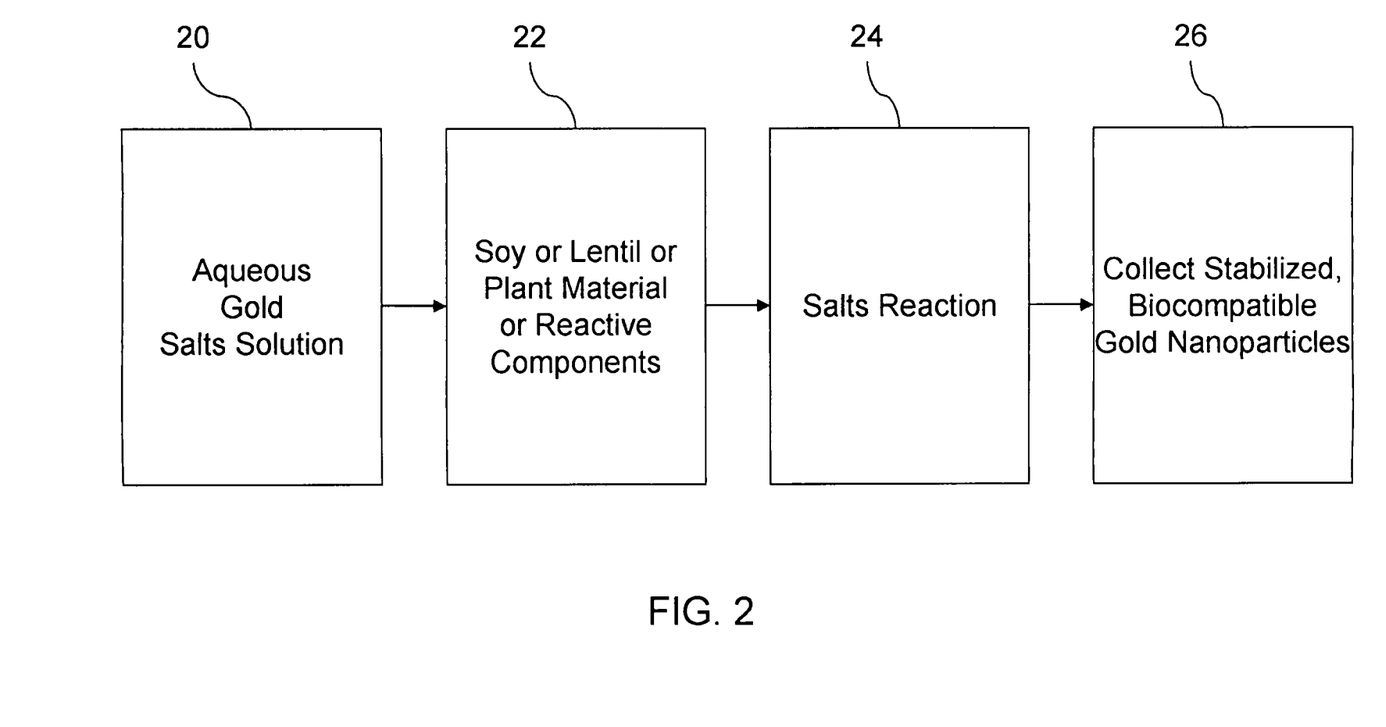
FIG. 2 illustrates a preferred method of fabricating a stabilized, biocompatible gold nanoparticle of the invention.

FIG. 2 illustrates a preferred method of fabricating a stabilized, biocompatible gold nanoparticle of the invention. In FIG. 2, an aqueous solution containing gold salts is provided 20. The aqueous solution is mixed 24 with soy or lentil plant material or specific reactive phytochemical extracts of such materials. Experiments consistent with the methods of FIG. 2 successfully produced well-defined spherical stabilized, biocompatible gold nanoparticles, by simple mixing of soybeans to an aqueous solution of sodium tetrachloro aurate. Better success was achieved by first extracting reactive soy extracts from soybeans. The stabilized, biocompatible gold nanoparticles generated through example soybeans-mediated experiments did not aggregate, indicating that the soybean phytochemicals including proteins serve as an excellent coating. The stabilized, biocompatible gold nanoparticles are generally non toxic because no external chemicals are used in the overall process.

Soy and Lentil Experiments

Detailed exemplary experimental procedures in preferred embodiment methods for making stabilized, biocompatible gold nanoparticles of the invention with Soy and Lentil are shown in Table 1:

TABLE 1

SUMMARY OF SOY AND LENTIL EXPERIMENTS

|  | Soya | Lentil |
|---|---|---|
| Solvent | Water | Water |
| Process time | Less than 1 min | 2 minutes |
| Reaction temperature | Room Temperature | Room Temperature |
| Size | 5-10 nm | 7-12 nm |
| Stability | High | High |
| Reproducibility | High | High |
| Biocompatibility | Suitable for in vivo | Suitable for in vivo |
| Eco friendly | Zero-chemicals used | Zero-Chemicals used |
| Scalability | Up to 2 liter | Up to 1 liter |

Materials

Sodium tetrachloroaurate and aurochloric acid were obtained from Aldrich Chemicals and used without further purification. soybeans and lentils were obtained from several geographic locations. Organic forms of these spices were obtained from authentic growers.

Reaction Procedures with Soybeans:

Stabilized, biocompatible gold nanoparticles nanoparticles were prepared by suspending 1-1.5 gm of soybeans in 6 ml of doubly ionized (DI) water. To this suspension 0.1 ml of 0.1M NaAuCl$_4$ solution was added. The color of the solution changes from light yellow to dark purple within 12-24 hours indicating the formation of stabilized, biocompatible gold nanoparticless (AuNP-Soy). The reaction is complete in 24 hours. The reaction can be expedited by microwave heating, and in the experiments this was demonstrated by heating the solution in a microwave for 5-10 seconds. The pH of the AuNP-soy solution is 3-4 and can be adjusted to physiological pH by adding 0.1 ml of phosphate buffer concentrate (pH 7) to whole volume. The nanoparticles generated by using Soybean are stable for over a period of 4 weeks. Further stabilization of gold nanoparticles generated from Soy was achieved by adding 0.2 ml of gum Arabic solution.

Figure 3:
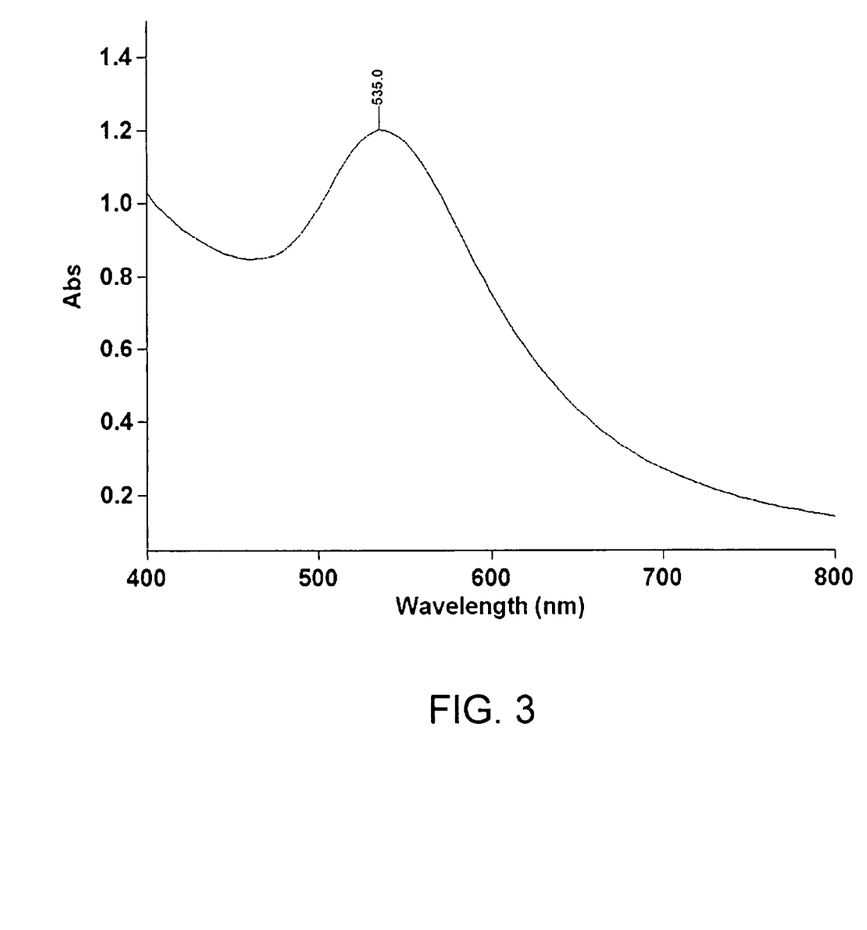
FIG. 3 is a measured UV-visible spectrum of stabilized, biocompatible gold nanoparticles of the invention produced in experiments with a coating generated by soy.

The formation of AuNP-Soy nanoparticles was confirmed by the characteristic plasmon resonance. FIG. 3 shows the plasmon resonance band, as shown in the ultra violet spectrum.

In Vitro Stability Studies of AuNP-Soy Gold Nanoparticles

In vitro stability studies were performed by challenging 0.5 ml of AuNP-Soy solutions in aqueous media with 0.5 ml each of 0.2M Cysteine, 0.2M Histidine and 0.2M Human Serum Albumin (HSA) solutions. The stability and the identity of AuNP-Soy were measured by recording UV absorbance at 2 hrs through 7 days. The plasmon resonance band at 535 nm confirmed the retention of nanoparticulates in all the above mixtures. Additionally in vitro stability measurements included challenging 0.5 ml of AuNP-Soy solutions in aqueous media with 0.5 ml of 35% saline. TEM measurements inferred the retention of the nanoparticulate composition in all the above in vitro studies.

Soy Extract Experiments

Materials and Methods

Chemicals were procured from standard commercial vendors: NaAuCl$_4$ (Alfa-Aesar); proteins, isoflavones, and sugars (Sigma-Aldrich). Size, charge, and morphology of gold nanoparticles generated from Soybeans and Soybean extracts were determined by three independent techniques/Transmission Electron microscopy (TEM), Differential Centrifugal Sedimentation (DCS, Disc Centrifuge, CPS Instruments), and Dynamic light scattering (DLS) methods (Malvern Instruments Ltd, USA) were employed. Transmission electron Microscope (TEM) images were obtained on JEOL 1400 transmission electron microscope (TEM), JEOL, LTD., Tokyo, Japan. TEM samples were prepared by placing 5 µL of gold nanoparticle solution on a 300 mesh carbon coated copper grid and the solution was to sit for five minutes; excess solution was removed carefully and the grid was allowed to dry for an additional five minutes. The average size and size distributions of gold nanoparticles were determined by processing of the TEM images using image processing software such as Adobe Photoshop (with Fovea plug-ins). DCS technique which was used to measure sizes was obtained on DC 24000, CPS Instruments Inc. USA. The hydrodynamic radius and the zeta potential were obtained on Zetasizer Nano S90, Malvern Instruments Ltd. USA. The absorption measurements were carried out using Varian Cary 50 UV-Vis spectrophotometers with 1 mL of gold nanoparticle solution in disposable cuvvettes of 10 mm path length.

Synthesis by Direct Reduction of Tetrachloroaurate with Soybeans (Soy-AuNP-1)

Gold nanoparticles were prepared by suspending 3 g of Soybeans in 10 mL of doubly ionized (DI) water for 2 h. To this suspension, 0.3 mL (0.289 mm) of 0.1 m NaAuCl$_4$ solution was added and the mixture was stirred at 25° C. for 4 h. The color of the supernatant solution changed from light yellow to dark purple indicating the formation of gold nanoparticles (Soy-AuNP-1). Soybeans were removed from the solution by decanting the solution followed by filtration through a 5 micron filter. The natural pH of the Soy-AuNP-1 solution was found to be 4 and was further adjusted to physiological pH by adding 0.1 mL of 10× phosphate buffer concentrate (pH 7) to the whole volume. The identity of Soy-AuNP-1 was confirmed through observations of plasmon resonance band at 540 nm in UV-Visible absorption measurements. The size distribution of Soy-AuNP-1 was inferred through detailed transmission electronic microscopic (TEM) and DCS, Disc Centrifuge techniques. In vitro stability studies in various media as described below have confirmed that these nanoparticles are stable over long periods of time (over two weeks) suggesting that the proteins in Soybeans have provided effective coating on AuNPs.

Preparation of Soybean Extract

Organic Soybeans purchased from a local grocery shop were used in all the experiments. Soybeans (8 g) were washed with DI water to remove any contaminant or dust particles. Soybeans were incubated in 50 mL of DI water at 25° C. for 72 h time period. The supernatant was decanted and centrifuged at 8000 rpm for 10 min at 25° C. The supernatant was stored at 4° C. and was used within 3 days for subsequent gold nanoparticle synthesis.

Synthesis Using Soybean Extract (Soy-AuNP-2)

Soybean extract as described above was used as phytochemically-derived reducing agents for the generation and stabilization of gold nanoparticles. In a typical experiment, 4 mL of Soybean extract was diluted to 8 mL in DI water and was heated up to 95° C. for 3 min. To this solution, 100 μL of $NaAuCl_4$ (0.1 m) was added and further heated to 95° C. with constant stirring for 5 min. The color of the mixture turned from pale-yellow to purple-red within 5 minutes indicating the formation of gold nanoparticles (Soy-AuNP-2) and the reaction mixture was further stirred for 2 hours at 25° C. to ensure complete reaction. Formation of gold nanoparticles was monitored by UV-Vis absorption spectroscopy. Plasmon resonance band at 540 nm indicated the formation of gold nanoparticles. TEM measurements confirmed the size distribution of gold nanoparticles. In vitro stability studies in various media as described below have confirmed that these nanoparticles are stable over long periods of time (over two weeks) suggesting that the proteins in Soybeans have provided effective coating on AuNPs.

Fractionation of High and Low Molecular Weight Fractions of Soybean Extracts

Soybean extract was further purified and concentrated using 5 kDa centrifugal filter devices (Centricon Plus-20). The centrifuge tube filled with 6 mL of Soybean extract was centrifuged at 4000 rpm for 10 min. The separated low and high molecular weight fractions were further diluted to a total volume of 8 mL with DI water and were used as such for the generation of gold nanoparticles.

Synthesis Using High Molecular Weight Proteins of Soybean Extract (Soy-AuNP-3):

To a 20 mL vial was added 8 mL of high molecular weight Soybean protein fraction (>5 kDa) obtained using Centricon Plus-20 centrifugal filter device. It was heated to 95° C. with continuous stirring for 3 min. To the stirring mixture was added 100 μL of 0.1 m $NaAuCl_4$ solution (in DI water) and further heated for 5 more min. The reaction mixture was further stirred for an additional 15 minutes at 25° C. Formation of gold nanoparticles was monitored by UV-Vis absorption spectroscopy. Plasmon resonance band at 540 nm indicated the formation of gold nanoparticles. TEM measurements confirmed the size distribution of gold nanoparticles and showed that the high molecular weight proteins.

Synthesis Using Low Molecular Weight Protein Fractions of Soybean Extract (Soy-AuNP-4)

To a 20 mL vial was added 8 mL of low molecular weight fraction obtained using Centricon Plus-20 centrifugal filter device. It was heated to 95° C. with continuous stirring for 3 min. To the stirring mixture was added 100 μL of 0.1 m $NaAuCl_4$ solution (in DI water) and further heated for 5 more min. The reaction mixture was further stirred for an additional 15 minutes at 25° C. This reaction resulted in the formation of dark-purple precipitate due to aggregation of gold nanoparticles. This observation suggests that low molecular weight fractions of Soybean extracts are capable of reducing Au(III) to the corresponding gold nanoparticles, however, the low molecular weight coatings do not form a sufficient coating around the gold nanoparticles to provide stability against aggregation. Thus, while the low molecular weight protein fractions can be used to form nanoparticles, they are not preferred as the coating that forms around the particles is a low quality coating.

Attempted Synthesis of Using Carbohydrates

To a 20 mL vial was added 0.0544 g of sucrose, 0.0064 g of raffinose, 0.0064 g of stachyose, followed by the addition of 8 mL of doubly ionized water (DI). The reaction mixture was heated to 95° C. and stirred continuously for 3 min. To the stirring mixture was added 100 μL of 0.1 m $NaAuCl_4$ solution (in DI water) and further heated for 5 more min. The reaction mixture was further stirred for an additional 15 minutes at 25° C. The progress of the reaction was monitored by UV-Vis absorption spectroscopy. Broad uncharacteristic bands in the 500-550 nm region indicated that the gold nanoparticles are aggregated and that carbohydrates initiate gold nanoparticle formation but provide no sufficient coating around the nanoparticles to render stability against aggregation. Thus, while carbohydrates can be used to form nanoparticles, they are not preferred as the coating that forms around the particles is a low quality coating.

Attempted Synthesis Using Isoflavones

To a 20 mL vial was added 0.012 g of gum Arabic (GA), followed by the addition of 0.47 mg of genistein, 0.3 mg of diadzein and 8 mL of doubly ionized water (DI). The reaction mixture was heated to 95° C. and stirred continuously for 3 min. To the stirring mixture was added 100 μL of 0.1 m $NaAuCl_4$ solution (in DI water) and further heated for 5 more min. The reaction mixture was further stirred for an additional 15 min at 25° C. UV spectrophotometric analysis of the reaction mixture indicated that there was no formation of gold nanoparticles, suggesting that isoflavones have no role or a very limited role a limited role in the reduction of Au (III) to nanoparticles.

In Vitro Stability Studies of Soy-AuNP-2

In vitro stability of Soy-AuNP-2 against aggregation was tested by mixing nanoparticle solutions to aqueous solutions of NaCl, histidine, human serum albumin (HSA) and bovine serum albumin (BSA) solutions. Briefly, 0.5 mL of Soy-AuNP-2 was added to 0.25 mL aliquots of 10% NaCl, 0.2 m histidine, 0.5% BSA or 0.5% HSA respectively.

The stability of Soy-AuNP-2 was also tested in pH 5, 7 and pH 9 phosphate buffer solutions. The stability and the identity of Soy-AuNPs were measured by recording UV absorbance at 24 hrs. The plasmon resonance band at 530 nm confirmed the retention of nanoparticulates in all the above mixtures.

SDS-PAGE Analysis of Soybean Extract and Soy-AuNP-2 Supernatant

Soybean extract prepared by soaking Soybeans for 72 h was used for the synthesis of gold nanoparticles. Nanoparticles contained in Soybean protein extracts were centrifuged at 20000×g. Post centrifugation, 1.8 mL of supernatant was concentrated using 3 kDa centricon filters to 0.3 mL. In separate micro centrifuge tubes, 50 μL of each of Soybean extract and gold nanoparticle supernatant were mixed with equal volume of 2× laemmli sample loading buffer (Biorad) with 2-mercapto ethanol (Sigma) and were heated at 95° C. for 10 min and 25 μL of each of the samples were resolved on a 4-20% tris-Glycene minigel (Biorad). One well of the gel was loaded with 10 μL of standard protein molecular weight marker (Biorad) and subsequently the gel was stained with Coomassie brilliant blue stain and scanned using Epson 4990 photo scanner.

Cell Culture

Human fibroblasts primary cultures were obtained as a gift from Prof Cris Lorson, Bond Life Science Centre, University of Missouri-Columbia. Fibroblast cells were maintained in DMEM with 10 pgmL$^{-1}$ phenol red, 10 mm HEPES, 100 units mL$^{-1}$ penicillin, 100 pgmL$^{-1}$ streptomycin, and 10% donor bovine serum (maintenance medium).

MTT Cytotoxicity Assay:

For the cytotoxicity evaluation of Soy-AuNP-2, MTT assay was performed as described by manufacturer (ATCC, USA). Briefly, 2×10$^4$ cells at the exponential growth phase were seeded in each well of a flat-bottomed 96-well polystyrene-coated plate and were incubated for 24 h in $CO_2$ incubator at 5% $CO_2$ and 37° C. Series of dilutions with 25, 50, 125 and 165 μm of these nanoparticles (gold atoms) were made in the medium. Each concentration was added to the plate in pentaplet manner. After 24 h incubation, 10 μL per well MTT (stock solution 5 mgmL$^{-1}$ PBS)(ATCC, USA) was added for 24 h. Formosan crystals were dissolved in 100 μL detergent. The plates were kept for 18 h in dark at 25° C. to dissolve all the crystals and the intensity of color progression was measured by micro plate reader (Dynastic MR 5000, USA) operating at 570 nm. Wells with complete medium, nanoparticles, and MTT, but without the cells were used as blanks. Untreated cells were considered as 100% viable.

Comparing Synthesis Methods

Soybean extract obtained by soaking Soybeans in deuterated water ($D_2O$) indicated that phytochemicals from Soybeans are extracted at very slow rates in aqueous media. Therefore, pre-extraction of the soy extracts prior to the reaction with gold salts provides for more efficient production of gold. Extracts prepared via incubation of Soybeans in DI water were used within 3 days for subsequent gold nanoparticle synthesis. The size of the Soy-AuNPs is found to be 15±4 nm as measured from the TEM images Role of Phytochemicals The main phytochemicals present in Soybeans consist of water soluble proteins (globulins and albumins), carbohydrates (sucrose, raffinose, and stachyose), saponins, isoflavones and amino acids. The water soluble proteins including glycinin (11s), β-conglycinin (7s) and trypsin inhibitor (2s) are of interest in their role in the overall reduction reactions of $NaAuCl_4$. The wxperiments systematically investigated the roles of proteins, sugars, antioxidants and various phytochemicals for the generation and stabilization of AuNPs through independent experiments.

Role of Soybean proteins

In order to understand the chemical propensities of various Soybean proteins to reduce $NaAuCl_4$ to the corresponding gold nanoparticles, the experiments that separated water-soluble Soybean proteins into low molecular weight (less than 5 kDa) and high molecular weight (higher than 5 kDa) fractions using Centricon Plus-20 centrifugal filter devices. The high molecular weight fractions, at 9° C., when mixed with $NaAuCl_4$ produced gold nanoparticles within 10 min. The corresponding reactions with the lower molecular weight fractions also resulted in the production of gold nanoparticles, but with poor stability toward aggregation. These results suggest that both the high and low Molecular weight fractions possess high kinetic propensity to initiate reduction of $NaAuCl_4$ to the corresponding nanoparticles. However, high molecular weight proteins, in addition to their efficacy for reduction, demonstrated their ability in providing a sufficient coating on the gold nanoparticles. The amino acids present in both the high and low molecular weight fractions are presumably responsible for the formation of gold nanoparticles.

From the fractions experiments and from information developed by others regarding the role of amino acids such as L-tryptophan, L-tyrosine, L-arginine, L-lysine, L-aspartic acid and small peptides, such as glycyl-L-tyrosine, (see, S. K. Bhargava, J. M. Booth, S. Agrawal, P. Coloe, G. Kar, *Langmuir* 2005, 21, 5949), the present inventors believe that that higher molecular weight Soybean proteins have distinct dual roles in reduction of Au(III) with subsequent stabilization of gold nanoparticles. While understanding of the mechanism is not necessary to practice the present invention, the disulfide bonds in the trypsin inhibitor (2s) proteins along with the Glycinin (11s) and β-Conglycinin (7s) appear to be important for providing a robust coating on the gold nanoparticles that shields the particles against aggregations and thus rendering them excellent in vitro stability.

Figure 4:
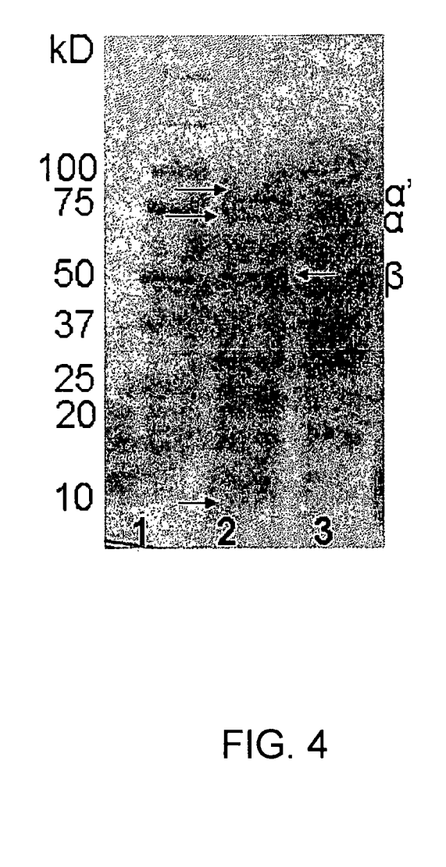
FIG. 4 is SDS-PAGE profile of soy proteins including a lane 1 showing a standard molecular weight marker, a lane 2 showing a 72 h soaked soybean extract, and a Lane 3 showing an esperiemental Soy-AuNP-2 (soy gold nanoparticles experiment 2) supernatant.

Specific soybean proteins potentially responsible for both generation and creation of robust coating on AuNPs were investigated via sodium dodecyl sulfate-polyacrylamide gel elecrophoresis (SDS-PAGE) analysis. These experiments involved the analysis of the presence of various proteins in (i) Soybean extract and (ii) Soy-AuNP-2 supernatants. Soy-AuNP-2 supernatant was obtained by centrifugal separation of AuNPs from Soy-AuNP-2. In these experiments, total proteins from Soybean extract and Soy-AuNP-2 supernatants, were resolved on a 4-20% Tris-Glycine minigel followed by commassie brilliant blue staining. As shown in FIG. 4, lane 1 corresponds to the standard protein marker, lane 2 corresponds to the total proteins from Soybean extract, and lane 3 represents Soy-AuNP-2 supernatant (Soybean proteins leftover after centrifugal removal of AuNPs). Comparisons of lane 2 and lane 3 revealed that the bands corresponding to 51 kDa and 80 kDa in lane 2 are absent in lane 3. It is important to note that polypeptides in the molecular weight range of 51-80 kDa are produced when the Soybean protein β-conglycinin degrades. The disappearance of 51 kDa and 80 kDa bands from Soybean protein extracts, post gold nanoparticles synthesis, suggests that these polypeptides are involved and fully consumed in both the generation and stabilization of gold nanoparticles.

From the SDS page results and the experiments described above, it is clear that Soybean extracts produced by soaking Soybeans in aqueous media for over 72 show the presence of large molecular weight proteins in good abundance. These large molecular weight proteins are effective in creating a robust coating over gold nanoparticles. Gold nanoparticles generated by using preformed Soybean extracts exhibited unprecedented in vitro stability beyond 3 months in experiments. Such stability is very important for the commercial use and packaging of particles in test kits for diagnostic and therapeutic medical techniques and for conducing diagnostic and therapeutic tests.

Role of Isoflavones Genistein, and Diadzein

The roles of isoflavones, genistein, and diadzein were investigated through the reactions of individual phytochemical extracts with $NaAuCl_4$. Poor aqueous solubility of both genistein and diadzein was a major experimental difficulty in these reactions. A mixture of both dimethyl sulfoxide and water was used as solvents to dissolve genistein (or diadzein). However, the reactions of genistein (or diadzein) with $NaAuCl_4$ at 25° C. or at higher temperatures did not result in the formation of AuNPs. These results indicate that genistein (or diadzein) present in Soybeans are presumably not involved in the overall reduction of $NaAuCl_4$.

However, it is also important to note that proton NMR studies of the extracts of Soybeans in $D_2O$ indicated the presence of genistein and diadzein. This shows that both genistein and diadzein as they are extracted directly from Soybeans into water may be associated with hydrophilic pockets of proteins/carbohydrates or other phytochemicals. Therefore, the cumulative reduction/stabilizing influence of both genistein and diadzein can not be ruled out from contributing to production of gold nanoparticles and stable coatings as they are chemically-available in Soybean extracts Role of Sugars Soybeans contain carbohydrates including sucrose (di-saccharide), raffinose and stachyose (oligosaccharides). The efficacy of individual carbohydrates for gold nanoparticles production via interactions with $NaAuCl_4$ in aqueous media was tested. Experiments with raffinose either at 25° C. or at higher temperatures did not result in the production of gold nanoparticles. Glucose and sucrose have been known to act as mild reducing agents for the reduction of $NaAuCl_4$ in aqueous media. However, such reduction reactions with sucrose and glucose proceed only at elevated temperatures resulting in incomplete conversions to gold nanoparticles with considerable amounts of unreacted $NaAuCl_4$. The experiments demonstrated that reactions of $NaAuCl_4$ with sucrose at 25° C. did not result in the production of gold nanoparticles. However, when this reaction was carried out at higher temperatures, partial conversions to gold nanoparticles were noticed and considerable quantity of unreacted tetrachloroaurate was observed. These results provide compelling evidence that Soybean proteins are the rate limiting phytochemicals that are directly involved in the reduction of $NaAuCl_4$ and that various carbohydrates and sugars present in Soybeans provide synergistic benefits to the overall reduction process Higher reaction temperatures presumably result in conformational changes of Soybean proteins and may also aid in opening up the protein structures, including Glycinin (11s) and β-Conglycinin (7s), so that the disulfide bonds become accessible to nanoparticles. Higher reaction temperatures are also important to utilize the synergistic reduction powers of carbohydrates within the Soybean phytochemicals.

Nanoparticle Characterization and Size Distribution

Size and Morphology

TEM measurements on Soy-AuNP-1 and Soy-AuNP-2 showed that particles are spherical in shape within the size range of 9-16 nm. Size distribution analysis of Soy-AuNPs confirm that particles are mono disperse The data is summarized in Table 2 nanoparticles are expected to cause substantial changes in the hydrodynamic radius of Soy-AuNPs. Hydrodynamic diameter of Soy-AuNP-2 as determined from DLS measurements gave a value of 61±1 suggesting that Soybean proteins are capped on gold nanoparticles. The measurement of charge on nanoparticles, Zeta Potential (ζ), provides crucial information on the stability of the nanoparticle dispersion. The magnitude of the measured zeta potential is an indication of the repulsive forces that are present and can be used to predict the long-term stability of the nanoparticulate dispersion. The stability of nanoparticulate dispersion depends upon the balance of the repulsive and attractive forces that exist between nanoparticles as they approach one another. If all the particles have a mutual repulsion then the dispersion will remain stable. However, little or no repulsion between particles, lead to aggregation. The negative zeta potential of −30±1 for Soy-AuNP-2 indicates that the particles repel each other and there is no tendency for the particles to aggregate (Table 2).

Cytotoxicity of Soy-AuNPs

The cytotoxicity of Soy-AuNP-2 using primary human fibroblast cultures as in vitro experimental models was studied. The cytotoxicity of Soy-AuNP-2 under in vitro conditions in human fibroblast cells was examined in terms of the effect of Soy-AuNPs on cell proliferation by the MTT assay. Fibroblast cells treated with 0, 25, 50, 125 and 165 μm concentrations of Soy-AuNPs [Au atoms] for 24 h were subjected to MTT assay for cell-viability determination. After 24 h of Soy-AuNP-2 treatment, cells showed more than 78% viability up to 165 μm concentrations of Soy-AuNP-2.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An environmentally friendly method for making biocompatible stabilized gold nanoparticles, the method comprising:

TABLE 2

PHYSICOCHEMICAL DATA PARAMETERS OF SOY-AUNPS

| | Size(nm) | | | Zeta Potential | In Vitro Stability | | | | |
|---|---|---|---|---|---|---|---|---|---|
| Sample | TEM | DLS[a] | CPS | (mV) | NaCl (10%) | Cysteine (0.5%) | Histidine (0.2 M) | pH 7 (PBS) | pH 9 (PBS) |
| Soy-AuNP-1 | 15 ± 4 | — | 17 ± 1 | — | U[b] | S | S | S | S |
| Soy-AuNP-2 | 15 ± 4 | 61 ± 1 | 10 ± 1 | −30 ± 1 | S[c] | S | S | S | S |

[a]Hydrodynamic Diameter.
[b]S: Stable.
[c]U: Unstable

DCS technique measures sizes of nanoparticles by determining the time required for nanoparticles to traverse a sucrose density gradient created in a disc centrifuge. Both the techniques, TEM and DCS, provide sizes of metallic-gold cores. Gold nanoparticulate sizes measured by TEM and DCS are in good agreement and are in the range 9-16 nm (Table 2). The dynamic light scattering method was employed to calculate the sizes of gold nanoparticles coated with proteins (hydrodynamic radius). The Soybean protein coatings on gold reacting soybean or lentil with gold salts in an aqueous solution lacking any other reactive chemicals;
permitting reaction of the gold salts with the soybean or lentil to continue to form stabilized, biocompatible gold nanoparticles.

2. The method of claim 1, wherein said reacting reacts soybeans.

3. The method of claim 1, wherein said reacting reacts lentil.

4. An environmentally friendly method for making biocompatible stabilized gold nanoparticles, the method comprising:
reacting soybean extract with gold salts in an aqueous solution lacking an other reactive chemicals;
permitting reaction of the gold salts with the soybean extract to continue to form stabilized, biocompatible gold nanoparticles, wherein the soybean extract comprises a supernatant obtained from incubating soybeans in distilled water.

5. The method of claim 4, wherein the supernatant comprises purified and concentrated supernatant that is purified to contain greater than 5 kDa high molecular weight protein fraction.

6. The method of claim 1, further comprising a step of heating the aqueous solution during said step of permitting reaction.

7. The method of claim 6, wherein said step of heating comprises microwave heating.

8. The method of claim 1, further comprising a step of adjusting the pH of the aqueous solution after said step of permitting reaction.

9. The method of claim 1, further comprising a step of adding a stabilizing agent to the aqueous solution after said step of permitting reaction.

10. The method of claim 9, wherein said stabilizing agent comprises gum Arabic.

11. The method of claim 1, wherein the gold salts comprises either sodium tetrachloaurate or aurochloric acid.

12. An environmentally friendly method for making biocompatible stabilized gold nanoparticles, the method comprising:
reacting soya or lentil with gold salts in an aqueous solution consisting essentially of the gold salts, water and the soya or lentil;
permitting reaction of the gold salts to continue form stabilized, biocompatible gold nanoparticles.

13. The method of claim 4, wherein the supernatant comprises purified and concentrated supernatant that is purified to contain greater than 5 kDa high molecular weight protein fraction.

14. The method of claim 4, further comprising a step of heating the aqueous solution during said step of permitting reaction.

15. The method of claim 14, wherein said step of heating comprises microwave heating.

16. The method of claim 4, further comprising a step of adjusting the pH of the aqueous solution after said step of permitting reaction.

17. The method of claim 4, further comprising a step of adding a stabilizing agent to the aqueous solution after said step of permitting reaction.

18. The method of claim 17, wherein said stabilizing agent comprises gum Arabic.

19. The method of claim 4, wherein the gold salts comprises either sodium tetrachloaurate or aurochloric acid.

20. An environmentally friendly method for making biocompatible stabilized gold nanoparticles, the method comprising:
reacting soybean extract with gold salts in an aqueous solution comprising the gold salts, water and the soybean extract and lacking any other reactive chemicals;
permitting reaction of the gold salts with the soybean extract to continue to form stabilized, biocompatible gold nanoparticles, wherein the soybean extract comprises a supernatant obtained from incubating soybeans in distilled water.

* * * * *

UNITED STATES PATENT AND TRADEMARK OFFICE
CERTIFICATE OF CORRECTION

PATENT NO. : 8,586,096 B2
APPLICATION NO. : 12/241904
DATED : November 19, 2013
INVENTOR(S) : Kattesh K. Katti et al.

It is certified that error appears in the above-identified patent and that said Letters Patent is hereby corrected as shown below:

On the Title Page:

Item (75) Inventors:

Page 1, Left Col., line 5-6  After "Raghuraman Kannan, Columbia, MO" please delete "(US)" and insert --(IN)-- therefor.

Page 1, Left Col., line 6-7  After "Kavita K. Katti, Columbia, MO" please delete "(US)" and insert --(IN)-- therefor.

Page 1, Left Col., line 7-8  After "Nripen Chanda, Columbia, MO" please delete "(US)" and insert --(IN)-- therefor.

Page 1, Left Col., line 8-9  After "Ravi Shukla, Columbia, MO" please delete "(US)" and insert --(IN)-- therefor.

Item (56) References Cited:

Page 2, Right Col., line 8  Please delete "medial" and insert --media-- therefor.

In the Specification:

Col. 2, line 40  Please delete "additional" and insert --addition-- therefor.
Col. 4, line 42  After "invention", please delete "interact".
Col. 8, line 37  After "very limited role", please delete "a limited role".
Col. 9, line 44  Please delete "wxperiments" and insert --experiments-- therefor.

In the Claims:

Claim 4, Col. 13, line 5  Please delete "an" and insert --any-- therefor.
Claim 12, Col. 14, line 1  After "continue", please insert --to--.

Signed and Sealed this
Twenty-ninth Day of April, 2014

Michelle K. Lee
*Deputy Director of the United States Patent and Trademark Office*